United States Patent
Kaspar et al.

(10) Patent No.: US 10,695,548 B1
(45) Date of Patent: Jun. 30, 2020

(54) GENE SILENCING IN SKIN USING SELF-DELIVERY SIRNA DELIVERED BY A MESO DEVICE

(71) Applicant: Transderm Inc., Salt Lake City, UT (US)

(72) Inventors: Roger L. Kaspar, Santa Cruz, CA (US); Tycho Speaker, Santa Cruz, CA (US)

(73) Assignee: TRANSDERM, INC., Salt Lake City, UT (US)

( * ) Notice: Subject to any disclaimer, the term of this patent is extended or adjusted under 35 U.S.C. 154(b) by 0 days.

(21) Appl. No.: 15/668,606

(22) Filed: Aug. 3, 2017

Related U.S. Application Data

(63) Continuation of application No. 14/181,582, filed on Feb. 14, 2014, now abandoned.

(60) Provisional application No. 61/764,928, filed on Feb. 14, 2013, provisional application No. 61/887,519, filed on Oct. 7, 2013.

(51) Int. Cl.
*A61M 37/00* (2006.01)

(52) U.S. Cl.
CPC .... *A61M 37/0015* (2013.01); *A61M 37/0092* (2013.01); *A61M 2037/0023* (2013.01); *A61M 2037/0061* (2013.01)

(58) Field of Classification Search
CPC .......... A61M 37/0015; A61M 37/0092; A61M 2037/0023; A61M 2037/0061
See application file for complete search history.

(56) References Cited

U.S. PATENT DOCUMENTS

| | | | | |
|---|---|---|---|---|
| 6,793,831 | B1 * | 9/2004 | Paul | B23K 20/023 148/194 |
| 8,252,755 | B2 * | 8/2012 | Yamada | C07H 19/00 514/44 A |
| 8,920,379 | B2 * | 12/2014 | Lee | A61M 37/0076 604/173 |
| 2004/0058882 | A1 * | 3/2004 | Eriksson | A61K 9/0021 514/44 R |
| 2006/0030538 | A1 * | 2/2006 | Hendriks | C12N 15/1137 514/44 A |
| 2007/0149470 | A1 * | 6/2007 | Kaspar | C12N 15/1131 514/44 A |

FOREIGN PATENT DOCUMENTS

| | | | |
|---|---|---|---|
| WO | WO2010/120111 A2 | 10/2010 | |
| WO | WO-2010120111 A2 * | 10/2010 | ........ A61M 37/0076 |

\* cited by examiner

*Primary Examiner* — Lauren P Farrar
(74) *Attorney, Agent, or Firm* — Nathan S. Smith; Kalpesh V. Upadhye; Morgan, Lewis & Bockius LLP

(57) ABSTRACT

The present invention is drawn to a low-cost "meso" device that is able to effectively deliver functional self-delivery siRNA to subject and inhibit expression of a gene in the subject as well as related methods. In particular, a method of transdermally delivering nucleic acid material to a subject is provided. The method includes adapting a motorized meso machine for delivery of nucleic acid material; introducing nucleic acid material into a chamber of the motorized meso machine; and contacting the motorized meso machine to a skin surface of a subject for a period of time sufficient to deliver the nucleic acid material into the skin surface of the subject.

20 Claims, 7 Drawing Sheets

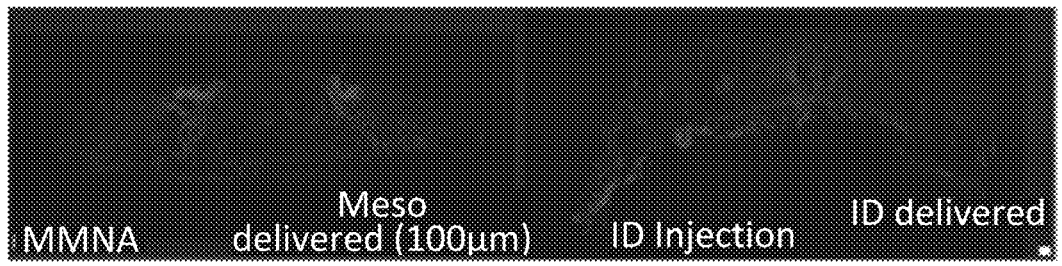
FIG. 2A
 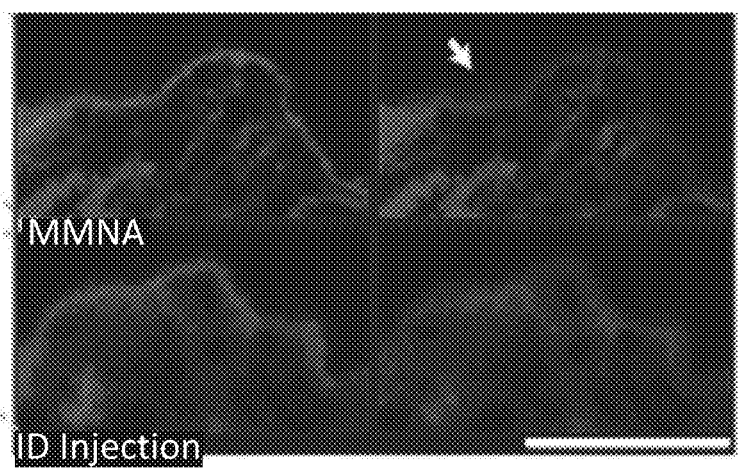
FIG. 2B  FIG. 2C
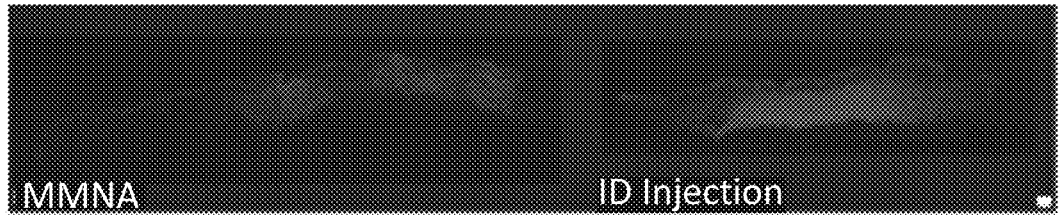
FIG. 2D

FIG. 2E  FIG. 2F

GENE SILENCING IN SKIN USING SELF-DELIVERY SIRNA DELIVERED BY A MESO DEVICE

This application is a continuation of U.S. patent application Ser. No. 14/181,582, filed Feb. 14, 2014, which claims the benefit of U.S. Provisional Patent Application Ser. No. 61/764,928, filed Feb. 14, 2013, and U.S. Provisional Patent Application Ser. No. 61/887,519, filed Oct. 7, 2013, each of which are incorporated herein by reference.

BACKGROUND

Of the 7,000 known monogenic disorders, approximately 2,000 affect the skin. While most of these are individually rare, together they represent a significant healthcare burden and afflict up to 1% of the population. For most of these disorders, there are no effective treatments that target the root cause of the problem. Nucleic acid therapies, including siRNAs, are a potential way to modify expression of disease genes in a controlled fashion, and hold real promise for improving patient lives. While traditional "small molecule" approaches to drug development have been a successful model for large pharmaceutical companies, the cost (on the order of a $1 billion) and the length of development time (10-12 years) limit their usefulness is rare inherited skin disorder. Identification of potent and selective siRNAs with limited off-target effects is now routine in many laboratories and the cost and time involved is a fraction of what is required for small molecule drug development. The missing piece in translating siRNA technology to the clinic is a robust, reproducible, economical and "patient-friendly" (i.e., little or no pain) delivery platform. Substantial effort has been invested in a variety of delivery technologies, with increasing success. However, the complexity and cost may limit clinical translation and patient compliance. For example, the first administration of siRNA to skin, and the first siRNA to target a mutant gene, was for pachyonychia congenita, a rare genodermatoses caused by mutant keratin alleles. The intradermal injection of TD101 siRNA (targets a single nt mutation [N171K] in the keratin 6a gene) resulted in improvement in the keratoderma and lesion pain, but the painfulness of the intradermal injection necessitated use of oral pain medication and a regional nerve block and prevented further enrollment in the clinical trial.

BRIEF DESCRIPTION OF DRAWINGS

FIG. 2A shows Cy3 labeled sd siRNA distribution in mouse flank skin treated by intradermal injection with a motorized microneedle array device loaded with 50 µL 0.1 mg/mL Cy3-labeled sd-siRNA. These sections of hairless mouse flank skin show breaches in the epidermis center of the injection site. The individual images were stitched together using ICE software.

FIG. 2B shows magnification (10x) of the meso-treated and intradermally-injected skin.

FIG. 2C shows further magnification of images from 2B showing diffusion of the Cy3-labeled siRNA in the epidermis originating from the needle penetration site (arrow). Left panels: 4'6-diamidino-2-phenylindole and Cy3 overlay; right panels: Cy3 alone.

FIG. 2D shows distribution of fluorescently labeled sd-siRNA in human abdominoplasty skin. Skin breaches due to penetration of the motorized microneedles are seen in their entirety using a x5 objective. Intradermally injected skin (50 µL of 0.1 mg/ml Cy3-labeled sd-snRNA) was similarly sectioned and imaged.

FIG. 2E shows magnification of treated skin.

FIG. 2F shows further magnification of the images from 2E shows diffusion of the Cy3-labeled sd-siRNA in the epidermis originating from the needles penetration site (arrow), whereas low levels of fluorescence are observed in the epidermis following intradermal injection. Left panels: 4'6-diamidino-2-phenylindole and Cy3 overlay; right panels: Cy3 alone. Nuclei are visualized by 4'6-diamidino-2-phenylindole stain (blue). Scale bar=200 µm.

SUMMARY

Figure 1A:
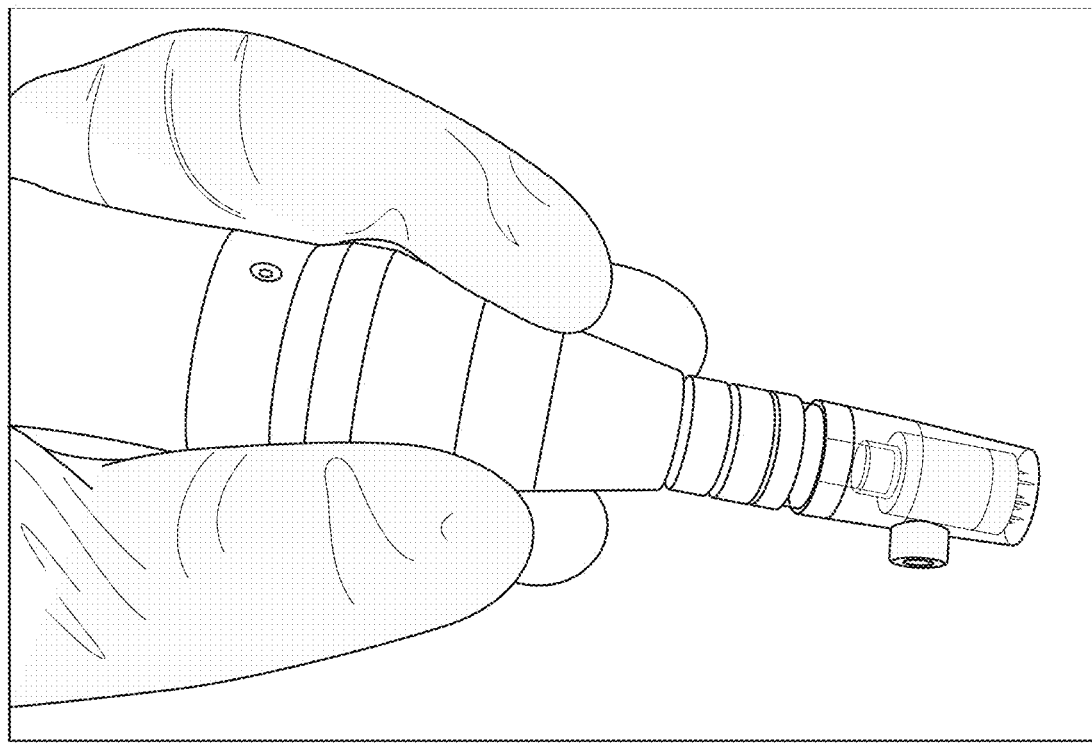
FIG. 1A shows a handheld motorized meso/microneedles array device.

As set forth herein, the present invention is drawn to a low-cost "meso" device that is able to effectively deliver functional self-delivery siRNA to a subject and inhibit expression of a gene in the subject as well as related methods. Accordingly, a method of transdermally delivering nucleic acid material to a subject is provided. The method includes adapting a motorized meso machine for delivery of nucleic acid material; introducing nucleic acid material into a chamber of the motorized meso machine; and contacting the motorized meso machine to a skin surface of a subject for a period of time sufficient to deliver the nucleic acid material into the skin surface of the subject.

DETAILED DESCRIPTION OF EXAMPLE EMBODIMENT(S)

Before the present devices, formulations, systems and methods for the delivery and use of nucleic acid materials are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It should be noted that, the singular forms "a," "an," and, "the" include plural referents unless the context clearly dictates otherwise. Thus, for example, reference to "a nucleic acid material" includes reference to one or more of such nucleic acids materials, and reference to "the motorized meso machine" includes reference to one or more of such motorized meso machines.

As used herein, "subject" refers to a mammal in having a condition for which rapamycin is a therapeutically effective treatment. In some aspects, such subject may be a human.

As used herein, the term "motorized meso machine" or "motorized meso device" are used interchangeably and refers to a motorized microneedle device that when placed on a skin surface can cause the microneedles to penetrate a skin surface due to vibration caused by the device. Such devices are well known in the cosmetic and dermal arts. A commercially available example of such a device is the Tiple-M or TriM by Bomtech Electronic Co, Seoul, South Korea).

As used herein, the term "about" is used to provide flexibility to a numerical range endpoint by providing that a given value may be "a little above" or "a little below" the endpoint.

The terms, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly.

As used herein, compounds, formulations, or other items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.5 to 10 g" should be interpreted to include not only the explicitly recited values of about 0.5 g to about 10.0 g, but also include individual values and sub-ranges within the indicated range. Thus, included in this numerical range are individual values such as 2, 5, and 7, and sub-ranges such as from 2 to 8, 4 to 6, etc. This same principle applies to ranges reciting only one numerical value. Furthermore, such an interpretation should apply regardless of the breadth of the range or the characteristics being described.

Unless otherwise defined, all technical and scientific terms used herein have the same meaning as commonly understood to one of ordinary skill in the art to which this invention belongs. Although any methods, devices and materials similar or equivalent to those described herein can be used in the practice or testing of the invention, representative methods, devices, and materials are described below.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, variants, modifications, and equivalents as may be included within the spirit and scope of the invention as defined by the appended claims.

Despite the development of potent siRNA molecules that effectively target genes responsible for skin disorders, translation to the clinic has been hampered by the difficulty of efficient delivery through the stratum corneum barrier into the live skin cells. Although intradermal injection of siRNA using hypodermic needles results in reproducible gene silencing, this approach is limited by the size of a single injection and is painful. The use of microneedle arrays is a less painful method for siRNA delivery, but limited payload capacity limits this approach to highly potent molecules. In the present case, a device that combines useful elements of both hypodermic needles and array technologies was used to effectively deliver functional siRNA to mouse and human skin. This commercially-available device utilizes an array of vibrating, adjustable-height needles, facilitating delivery of cargo solution through the stratum corneum with little to no pain. Treatment of both human and murine skin resulted in distribution throughout the treated skin (including the epidermis). Efficient silencing (58% reduction) of reporter gene expression was achieved in a transgenic reporter mouse skin model.

siRNAs are promising agents for treating monogenic skin disorders particularly those caused by dominant mutations, if delivery concerns can be overcome. The use of siRNAs as therapeutics has made substantial progress in recent years and clinical trials are underway for treatment of a variety of disorders in eye, liver, kidney and skin. Due to the accessibility of skin, direct injection of "naked" nucleic acids has been suggested as the most simple, safe and efficient delivery method. However, direct injections are limited to a highly localized region of the epidermis coincident to the injection site, and large number of injections may be needed to achieve uniform delivery and a therapeutic outcome.

The first siRNA used in skin, TD101, targeted a mutant version (N171K) of keratin 6a, which is one of the mutations responsible for the dominant negative monogenic skin disorder pachyonychia congenita (PC). TD101 was also the first siRNA used in the clinic to target a mutant gene. Improvements in PC symptoms were observed at the plantar site of siRNA intradermal injection in the single patient initially enrolled in the study, but not the paired injection site on the opposite foot that received vehicle alone. Intradermal injections of either siRNA or vehicle alone were accompanied by severe pain, necessitating nerve blocks as well as oral pain medication on the treatment days. Additional patients were not enrolled due to the intense pain associated with these injections. The intense pain associated with intradermal injection leads to the need to explore alternative "patient-friendly" delivery technologies (i.e. effective delivery of functional siRNA with little or no pain).

Multiple physical approaches have been reported in the literature to facilitate delivery across the stratum corneum barrier including ultrasound, erbium:YAG laser, gene gun (ref), iontophores is, electroporation and microneedles. Once the siRNA passes the stratum corneum barrier, however, the affected cells must still internalize the siRNA in a manner that allows for incorporation into the RNA-induced silencing complex (RISC). Naked siRNA is not normally taken up by keratinocytes in the absence of transfection unless the siRNA administration is accompanied with pressure ("pressure-fection"). It has been shown that covalent "self-delivery" modifications (including Dharmacon's Accell modifications), facilitate cellular uptake in vitro and in vivo without the need for tranfection reagents. Additionally, it has been previously reported that administration of these self-delivery siRNA by dissolvable microneedle arrays could reduce target gene expression up to 50% in both mouse and human skin models. The nearly 60% reduction in target gene expression reported herein delivering sd-siRNAs with the meso device warrants additional study for use in patients and represents an alternative path to using microneedle arrays for delivery across the stratum corneum barrier.

With the above in mind, the present invention is drawn to a low-cost "meso" device that is able to effectively deliver functional self-delivery siRNA to subject and inhibit expression of a gene in the subject as well as related methods. Accordingly, a method of transdermally delivering nucleic acid material to a subject is provided. The method includes adapting a motorized meso machine for delivery of nucleic acid material; introducing nucleic acid material into a chamber of the motorized meso machine; and contacting the motorized meso machine to a skin surface of a subject for a period of time sufficient to deliver the nucleic acid material into the skin surface of the subject. The adapting of the motorized meso device can include adjusting the depth of needle penetration for the device and/or adjusting the oscillation rate of the needles. It is noteworthy that it is theoretically possible that the "adapting" step of the claimed invention may not require any affirmative adjustment of the device, rather a mere checking of the settings of the device to assure that they are at the desired setting for a given application. In one aspect, the needles of the motorized meso machine includes deliver the nucleic acid material into the skin surface at a depth of about 25 microns to about 3 mm.

In one embodiment, the nucleic acid material delivered by the motorized meso machine can be siRNA. In another embodiment, the nucleic acid material can be sd-siRNA. In some aspects, it can be useful to utilize nucleic acid material that is suspended in a solution. In one embodiment, the nucleic acid material can be suspected in a PBS solution. Other solvents or liquid carriers known in the art to be compatible with nucleic acid material can also be used.

Once the motorized meso machine is applied loaded with the nucleic acid material, the machine can contact the skin of a subject being treated for a period of time sufficient to allow for delivery of the nucleic acid. In some embodiments, the period of time of contacting can be for a period of about 5 seconds to about 20 seconds. In another embodiment, the period of time can be about 7 seconds to about 15 seconds. The contacting can be repeated in the same skin area or can be repeated on other skin areas, e.g. adjacent skin areas in order to provide the desired delivery.

The disclosed invention provides a strong alternative to traditional microneedles and hypodermic needle injections.

EXAMPLES

The following examples are provided to promote a more clear understanding of certain embodiments of the present invention, and are in no way meant as a limitation thereon. The compositions may be suitably modified by a person skilled in the art. The following materials and methods were utilized in the Examples described herein.

Animals

Hairless mice (6-8 weeks old) were purchased from Charles River Laboratories (Wilmington, Mass.) and housed at TransDerm. Hairless Tg CBL/hMGFP mice were generated by breeding Tg CBL/hMGFP mice on a Hairless background and maintained at Stanford University. Animals were treated according to the guidelines of the National Institutes of Health (NIH), TransDerm and Stanford University.

siRNA

Unmodifed specific (CBL3 and non-specific siRNAs (TD101 K6a3'UTR.1 NSC4 and "self-delivery" Accell® specific (sd-CBL3 and non-specific (sd-TD101 sd-CD44 and Cy3-labeled (ref)) siRNAs containing Dharmacon-proprietary modifications allowing for cellular uptake without traditional transfection reagent) were synthesized by Thermo Fisher Scientific, Dharmacon Products (Lafayette, Colo.); Accell siRNAs are available commercially from this source.

Example 1—Delivery of siRNA Cargo into the Epidermis by the Meso Device

Figure 1B:
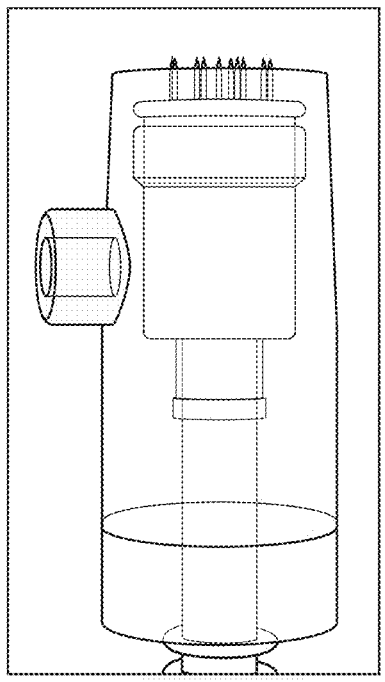
FIG. 1B shows the inner reservoir of the motorized microneedle array cartridge array contains 300 µL of a red dye solution for visualization, and shows the needles are set to protrude 0.1 mm beyond the edge of the chamber.
Figure 1C:
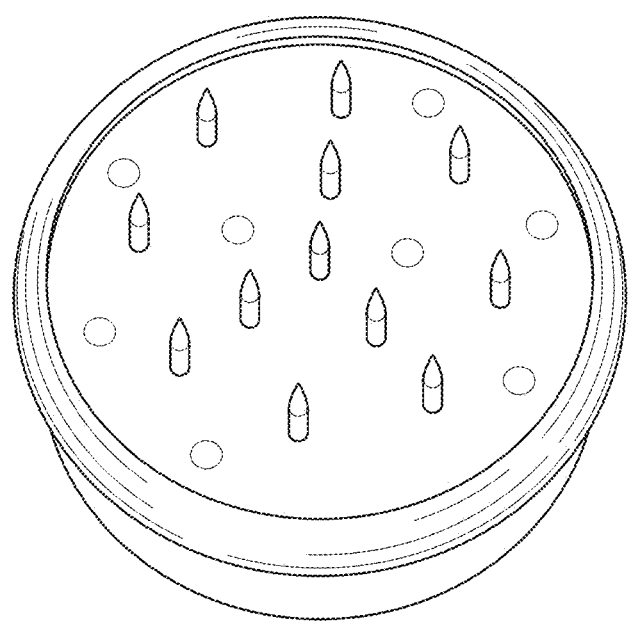
FIG. 1C shows channels intermittently located between the needles allow flow of solution onto the surface of the skin during treatment.

Despite the promise of siRNA for use as skin therapeutics, a major obstacle is delivery of these molecules through the stratum corneum barrier due to their size (~13,000 MW) and polyanionic nature. Meso devices can be used to deliver a variety of molecules across this barrier through direct penetration using vibrating needles that are provided as a single use sterile disposable cartridge (FIG. 1). As the depth of needle penetration can be adjusted, this device has the potential to deliver cargo to different skin types ranging from thin mouse skin (<50 um) to thick human plantar skin (>1 mm). Furthermore, the ability to adjust depth allows for deposition in the epidermis, avoiding the pain nerve fibers that are prevalent in the dermis.

Figure 5A:
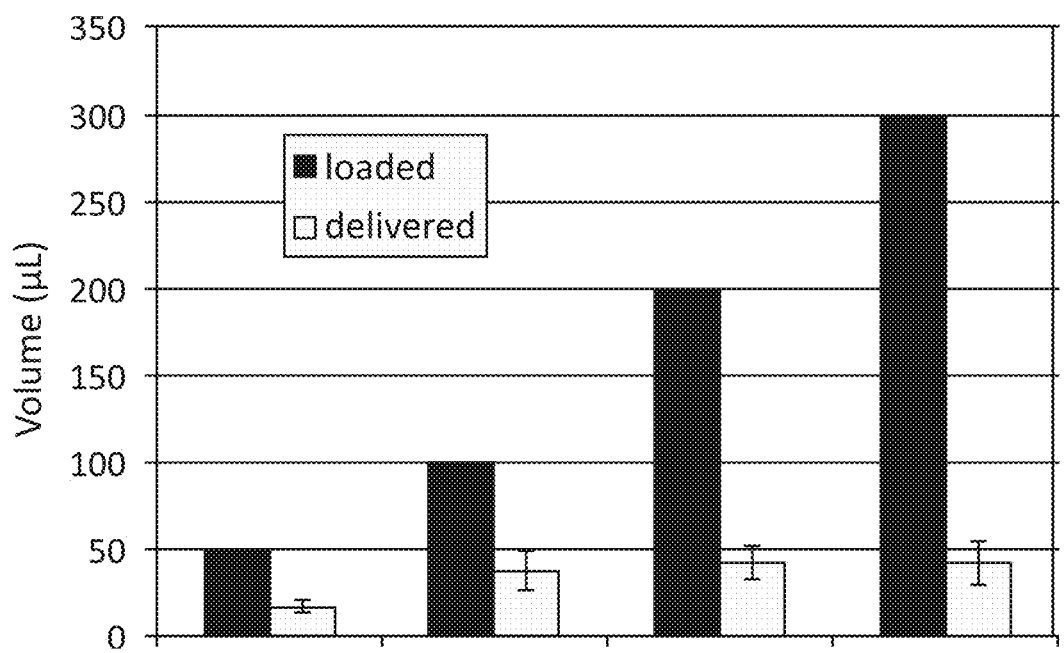
FIG. 5A shows a graphical representation of a procedure where the meso chamber was loaded with the indicated volume of PBS solution and applied to mouse flank skin at the 0.1 mm depth setting for 10 s. The solution remaining in the chamber and on the surface of the skin was collected and measured (red bars).
Figure 5B:
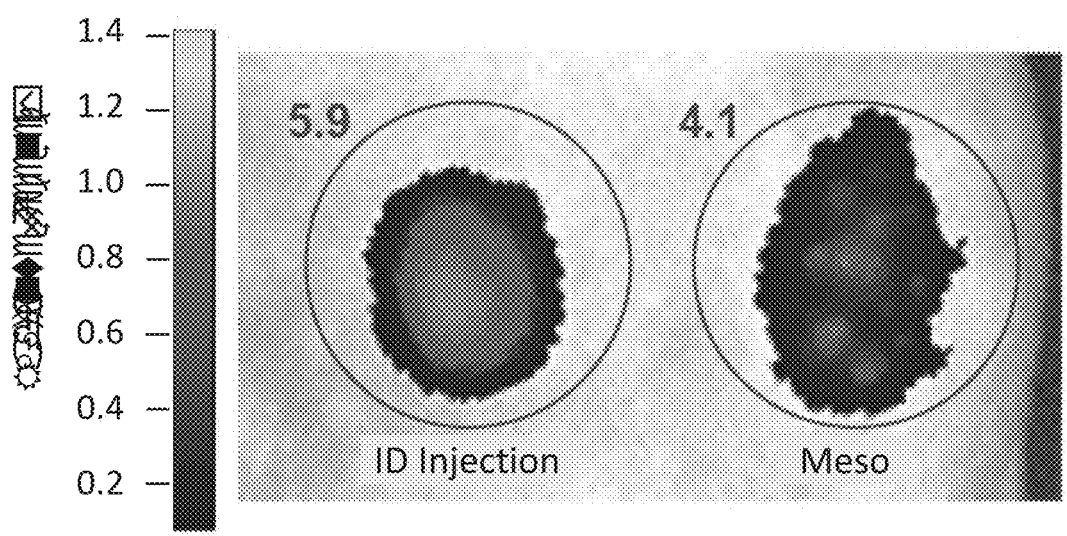
FIG. 5B shows images from the following procedure. To confirm the volume delivered as described in A, 50 µL of labeled siRNA was loaded in the chamber and an equivalent volume of the predicted delivery volume using the meso device (16 µL) was intradermally injected adjacent to the meso treatment site and imaged with the IVIS Lumina II.

To determine the amount of potential cargo that can be delivered to skin, the meso device was loaded with 50, 100, 200 or 300 μL of PBS solution. After application to murine flank skin for 10 s (set to deliver at a depth of 0.1 mm), the solution remaining in the meso device and on the surface of the skin was collected and measured and used to calculate the total volume delivered. Once a threshold volume of 100 μL was loaded into the device, adding additional solution did not result in increased cargo delivery (FIG. 5A). Thus, in mouse flank skin, a maximal delivered volume of 40 μL occurred when 100 μl of solution was loaded into the cartridge. In order to confirm that delivery was occurring, murine flank skin was treated with the meso device loaded with 50 μL of 0.1 mg/mL fluorescently-tagged sd-siRNA (Cy3-Accell siRNA, see Materials and Methods). The calculated volume delivered by meso (16 μL) of the same solution was then intradermally injected adjacent to the meso-treated area. Fluorescence was measured by in vivo imaging and resulted in similar intensities (FIG. 5B).

In order to visualize siRNA distribution in the skin, mice were sacrificed 1 h following treatment with the fluorescently-tagged siRNA, and the treated skin was embedded in OCT, sectioned (10 μm) and analyzed by fluorescence microscopy. Meso-assisted delivery resulted in a gradient of fluorescently-tagged siRNA distribution throughout treated area of the skin with peak intensity observed at the site of needle injection (FIG. 2A). Importantly, the bulk of fluorescent signal was observed migrating laterally through the epidermis from the needle penetration site (FIG. 2B). Intradermal injection of the fluorescently-tagged siRNA also resulted in distribution of signal throughout the dermis and epidermis (FIG. 2A and data not shown). The distribution of labeled sd-si-RNA in human skin was similarly analyzed (FIG. 2D). As in mouse skin, the fluorescent signal was observed in a gradient pattern from the site of needle penetration including lateral distribution through the epidermis (FIG. 2E, F). In contrast to the distribution pattern observed upon intradermal injection in mouse flank (FIG. 2C), less labeled siRNA was detected in the epidermis of the human skin following intradermal injection with a hypodermic needles (FIG. 2E, F), consistent with previous experiments in both human abdominal explant skin and mouse footpad skin.

Figure 3A:
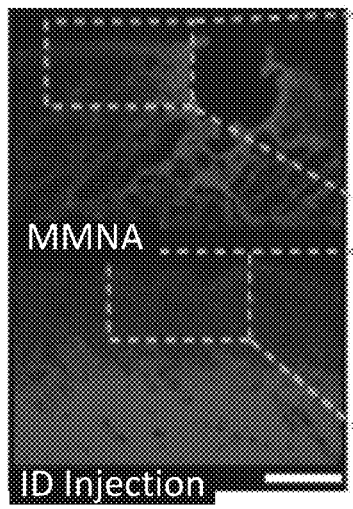
FIG. 3A shows a graphical representation of data showing that meso-assisted delivery of sd-siRNA inhibits targeted reporter gene expression from the following procedure. Hairless tg CBL/hMGFP mouse flank skin was treated daily with the meso device loaded with 50 µL 10 mg/mL CBL3 sd-siRNA or non-specific control sd-siRNA (sd-TD101) for 10 days. On day 11, the mice were sacrificed and the treated skin was excised for RTqPCR analysis and fluorescence imaging. Total RNA was isolated from the epidermis of the excised skin, reverse transcribed and hMGFP mRNA levels (relative to K14) were quantified in triplicate by qPCR. Bars indicate standard error.
Figure 3A:
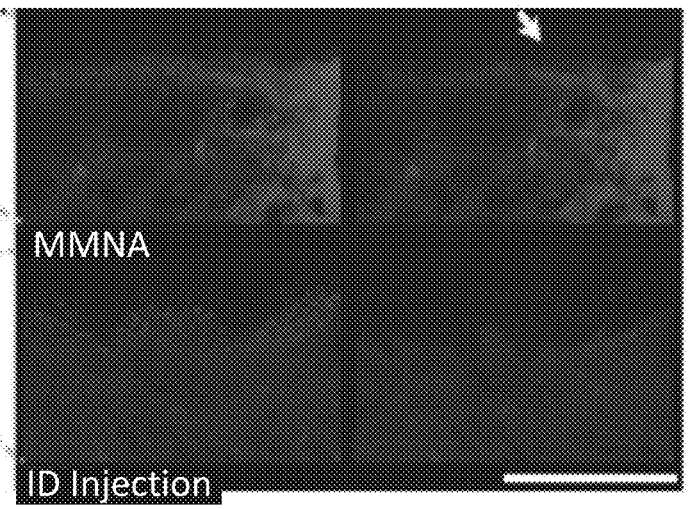
Figure 3A:
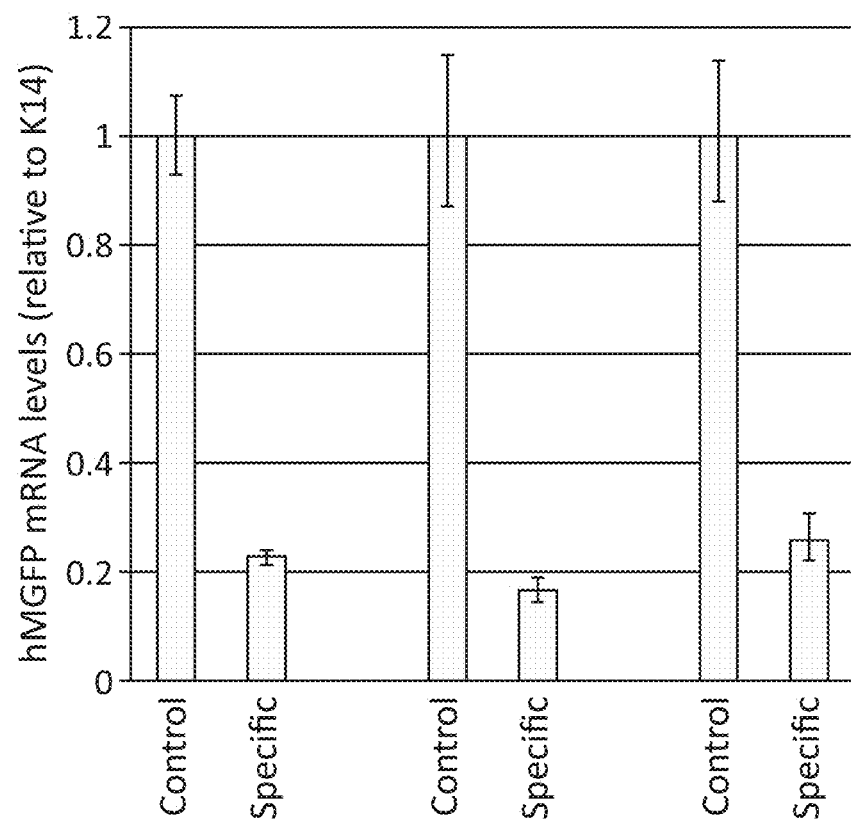
Figure 3B:
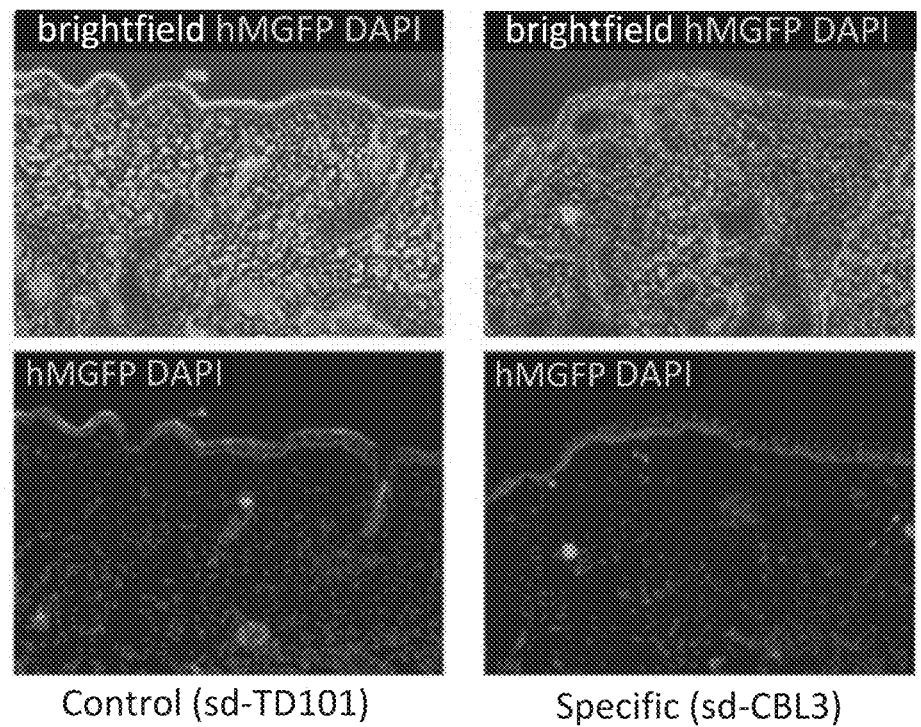
FIG. 3B shows representative fluorescence images (bottom) with bright field overlay (top) of frozen skin sections (10 µm) prepared from treated mice showed knockdown of hMGFP signal fluorescence signal in the skin treated with specific sd-siRNA over control sd-siRNA. Nuclei are visualized by 4',6-diamidino-2-phenylindole stain (blue). Scale bar is 100 µm.

Example 2—Silencing of CBL/hMGFP Reporter Gene in Transgenic Mouse Epidermis It has been previously reported silencing of a fluorescent reporter gene in a tg mouse skin model (Tg CBL/hMGFP) after administration of unmodified and self-delivery CBL3 siRNA by intradermal injection and microneedle application, respectively. In order to evaluate the ability of the meso device to deliver functional sd-CBL3 siRNA in this model, Tg CBL/hMGFP mouse flank skin was treated and reporter gene expression analyzed. Flank skin was treated every day for 10 days. On day 11, the mice were sacrificed and flank skin was excised for RNA isolation and histology. Reporter mRNA (CBL/hMGFP) levels were measured by RT-qPCR (FIG. 3A). A significant reduction (averaging 58±5%) of reporter expression was detected in skin treated with the specific CBL3 sd-siRNA compared to the contralateral flank skin treated with non-specific control sd-siRNA (sd-CD44 siRNA). This experiment was repeated comparing CBL3 sd-siRNA to non-specific sd-TD101 siRNA with similar results (data not shown). The decreased hMGFP levels were corraborated by fluorescence microscopy of CBL3 sd-siRNA-treated skin compared to control sd-siRNA treatment (FIG. 3B). Fluorescence images of hMGFP were overlaid with 4',6-diamidino-2-phenylindole (DAPI) and bright field images to locate the basal layer and stratum corneum.

Figure 4A:
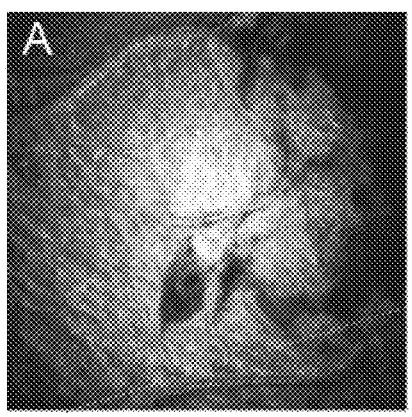
FIG. 4A-4C show confocal fluorescence imaging of Cy3-labeled sd-siRNA in human skin xenografts. A,B. Following meso assisted delivery (30-60 min) of 100 µL 0.5 mg/mL Cy3-labeled sd-siRNA (in Phosphate Buffered Saline, hereinafter "PBS") into human skin, reflectance (panel A) and red fluorescence (panel B, C) were imaged with the Lucid Vivascope system)
Figure 4B:
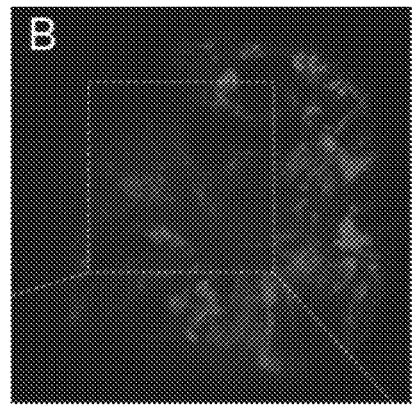
Figure 4C:
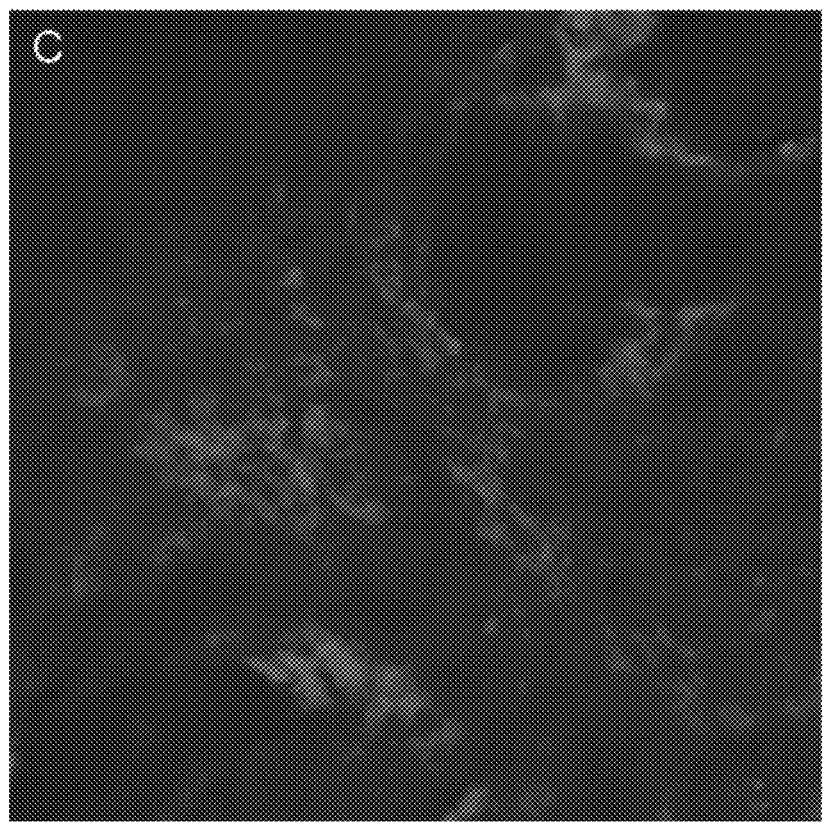
Figure 6A:
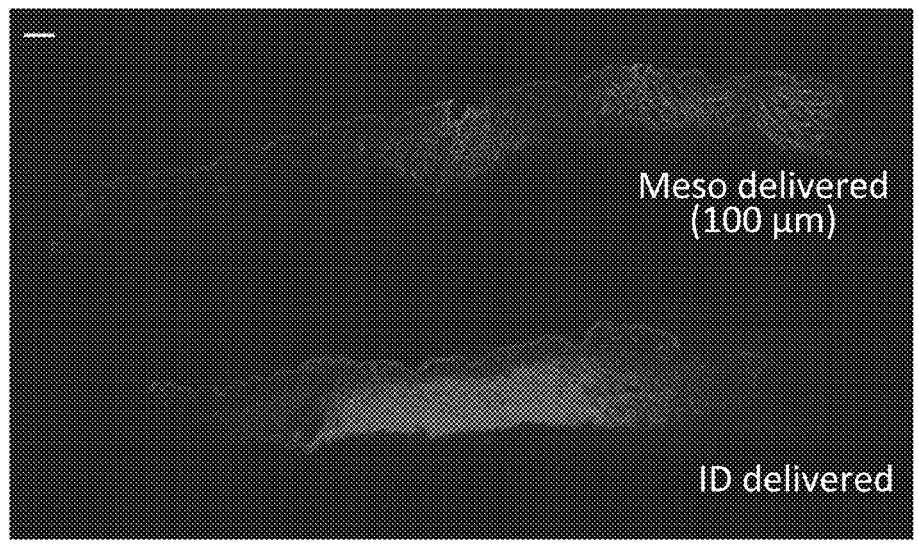
FIG. 6A shows distribution of fluorescently-labeled siRNA in frozen sections prepared from meso-treated skin, specifically, Cy3-labeled siRNA distribution in human skin. Human abdominoplasty skin was treated with the meso device loaded with 50 µL 0.1 mg/mL Cy3-labeled sd-siRNA (Accell) or injected intradermally with 50 µL of the same solution. Skin breaches due to meso needle penetration are seen in their entirety using a 5x objective as well as a distribution gradient in signal from the delivery site. Intradermally-injected skin was sectioned to the center of the injection and similarly imaged. The individual images (stitched together using ICE software, see Materials and Methods) show similar levels of fluorescence when comparing the meso-treated and ID-injected skin sites.
Figure 6B:
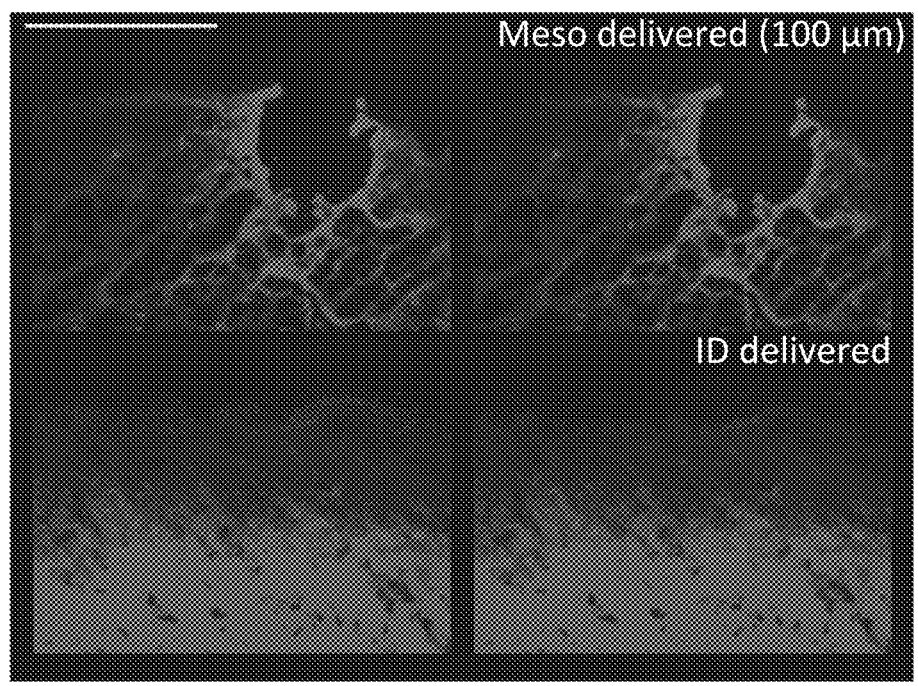
FIG. 6B shows magnification (10× objective) of the meso-treated skin showed diffusion of the Cy3-labeled siRNA in the epidermis originating from the needle penetration site, whereas low levels of fluorescence was observed in the epidermis following intradermal injection. Left panels: DAPI and Cy3 overlay; right panels: Cy3 alone. Scale bar=400 μm.

Example 3—Distribution of Fluorescently-Tagged siRNA Following Meso-Assisted Delivery in Human Skin In order to visualize delivery of sd-siRNA in a human model, freshly-obtained explant skin (from plastic surgery procedures) was treated for 10 s with the meso device set at a depth of 100 μm. 50 μL of 0.1 mg/mL Cy3-labeled sd-siRNA was delivered to skin for cryosectioning while 100 μL of 0.5 mg/mL Cy3-labeled sd-siRNA was delivered to skin for in vivo confocal imaging. For cryosectioning, the skin was embedded in OCT 1 h post-treatment, sectioned and imaged by fluorescent microscopy (FIG. 6A). Similar to delivery of labeled sd-siRNA to mouse skin, the fluorescent signal was observed in a gradient pattern from the site of needle penetration including diffusion laterally through the epidermis (FIG. 6B). Interestingly, lower signal was detected in the epidermis of intradermally-injected skin (FIG. 6B and data not shown).

siRNA distribution was also visualized in human skin using confocal imaging. Skin removed during a rhytidectomy procedure was treated with 100 μL 0.5 mg/mL Cy3-labeled sd-siRNA and imaged using the Lucid Vivascope 30-60 min post-treatment. Reflectance images collected at 658 nm show the needle penetration site (FIG. 4A) at 26 μm depth. Red fluorescence (ex. 532 nm; em. 607 nm) at 59 μm depth shows radial distribution from the needle penetration side (FIG. 4B) and interaction with individual cells (FIG. 4C).

Example 3—Meso-Assisted Delivery of Sd-siRNA

A Motorized Meso Machine (Triple M) was adapted for delivery of siRNA to mouse and human skin. sd-siRNA solution (up to 300 μL) was introduced into the chamber of the disposable meso needle cartridge using a standard P-200 pipet tip. For treating mice, a fold of skin was laid flat on a plastic surface and held in place with the tip of the meso device. With the meso device oriented vertically (perpendicular to the fold of skin) the device was turned on and held in place for 10 seconds. For treating human skin, fresh abdominal skin (obtained from abdominoplasty procedure) was manually stretched and pinned to a cork platform prior to treatment as described above.

Example 4—Histological Analysis of Fluorescently-Labeled Sd-siRNA Distribution in Murine and Human Skin Cy3-Accell Non-Targeting siRNA (Dharmacon Products, Thermo Fisher Scientific, Lafayette, Colo.) was loaded into the chamber of the meso device (50 μL 0.1 mg/mL). Mouse flank skin or de-identified human abdominal skin from an abdominoplasty procedure was treated as described above and imaged in an IVIS Lumina imaging system (Xenogen product from Caliper LifeSciences, Alameda, Calif.) using the 535 nm excitation and DsRed emissions settings (1-10 s acquisition time). The data were quantified using LivingImage software (Caliper LifeSciences) and presented as an overlay with the brightfield data. Fluorescent background from an untreated area of the same animal or tissue sample was subtracted and values were reported as radiant efficiency. Skin was then embedded in OCT and sectioned for analysis by fluorescence microscopy using a Zeiss Axio Observer Inverted Fluorescence Microscope equipped with Cy3 and DAPI filter sets as previously described.

Example 5—Confocal Microscopy of Fluorescently-Labeled Sd-siRNA Distribution in Murine and Human Skin Cy3-Accell Non-Targeting siRNA was loaded into the chamber of the meso device (100 μL 0.5 mg/mL). De-identified human facial skin from a face lift procedure was treated as described above and imaged using a modified Lucid VivaScope 2500 System (Lucid Inc., Rochester, N.Y.) 30-60 min following treatment as previously described. Briefly, image z-stacks were generated by image acquisition at successive z-depths using native VivaScan software (v. VS008.01.09), and then post-processed using public domain Fiji java-based image processing software, Images were acquired in reflectance mode using a 658 nm laser source, and duplicate stacks were acquired using a 532 nm excitation laser and with a long pass filter to collect 607 nm emission.

To increase the effective resolution of the VivaScope images, 10 nominal duplicate images were taken at each z-step, and these 10 image sets were averaged to produce z-step-averaged images, resulting in the final image stack. Because in vivo imaging is influenced by respiration and other minor subject motion, successive frames were co-registered using an affine transform; distributed with Fiji software as the StackReg plugin) prior to any frame-averaging. Images were further intensity-scaled to maximize contrast with the Fiji software using a global constraint such that the highest intensity 0.1% of image pixels in each frame were scaled to a pixel intensity value of 256.

Example 6—Meso-Assisted Delivery of Sd-siRNAs and Analysis of Gene Silencing

Two cohorts of anesthetized tg-CBL/hMGFP mice were treated with 50 μL of 10 mg/mL solution in PBS of either sd-CBL3 siRNA or a non-specific control sd-siRNA (CD44 or TD101 sd-siRNA) as described above every day for 10 days. The day following the last treatment, mice were euthanized and the treated area was excised for analysis by both fluorescence microscopy and RTqPCR as described in with the following modifications. The epidermis was separated from the dermis by incubation in dispase II (10 mg/mL in PBS, Roche, Indianapolis, Ind.) for 2-4 hours at 21° C. prior to RNA isolation.

Example 7—Histological Analysis of Treated Skin

To assess potential tissue damage due to penetration of the array microneedles alone versus inflammation caused by deposition of sd-siRNA, PBS, or sd-siRNA (in PBS) was administered to hairless tg-CBL/hMGFP mice with MMNA device. The skin was harvested 24 hours after treatment and immediately fixed in formalin and embedded in paraffin. Histology of the treated skin revealed areas consistent with needle penetration and associated skin damage. Acute inflammation was observed with prominent polymorphonuclear infiltrate in the papillary dermis extending down into, but not through the reticular dermal layer, primarily at eh site of needle penetration through the epidermis but also throughout the dermis. Scattered macrophages and chronic inflammatory cells were also present, consistent with classic wound healing, as would be expended from a standard hypodermic needle injection. Inflammation was generally localized around wounded regions. There were no visual differences in wound response in skin treated with vehicle alone as compared with skin treated with TD101 or CBL3 sd-siRNA (data not shown), suggesting that observed acute inflammation is not due to the presence of sd-siRNA.

Example 8—Analysis and Discussion of the Use of Meso-Devices to Deliver Sd-siRNA's Due to its accessibility, skin is an attractive target for siRNA therapeutics, and direct injection of "naked" nucleic acids are thought as simple, safe, and efficient delivery method. However, direct injections are limited to a highly localized region of the epidermis coincident with the injection site, and large number of injections may be needed to achieve the uniform delivery required for a favorable therapeutic outcome. Indeed, although some efficacy may result from intradermal injection of siRNA, generally the efficacy can be limited to the area immediately surrounding the plantar injection site. Further intradermal injections of either siRNA or vehicle alone are accompanied by severe pain, necessitating nerve blocks as well as oral pain medication before treatment. This pain is likely due, at least in part, to the large volume (up to 2 ml) of drug injected into the lesion. The high pressure required for siRNA delivery is also likely at least partially responsible for the intense pain experienced with these injections. Thus, the disclosed invention is an alternative "patient-friendly" (i.e. little or no pain) delivery technology.

For functional delivery, siRNA must not only transit the stratum corneum barrier, but also be internalized into cells in a manner that allows for incorporation into the RNA-induced silencing complex (RISC). In addition to direct injection with hypodermic needle, multiple physical approaches have been evaluated the reportedly facilitate delivery of nucleic acids across the stratum corneum barrier including ultrasound, erbium:YAG laser, gene gun, iontophoresis, electroporation, microneedles, and now motorized microneedles. However, unmodified nucleic acids are not normally taken up by keratinocytes in the absence of transfection agents unless the administration is accompanied with pressure ("pressure-fection"). Covalent "sd" siRNA modifications (e.g., Dharmacon's Accell modifications) facilitate a cellular uptake in vitro and in vivo without the need for transfection reagents. Administration of sd-siRNA by dissolvable microneedle arrays can reduce target gene expression up to 50% in both mouse and human skin models. The nearly 90% average reduction in target gene expression provided by the devices and techniques disclosed herein exceeds with the threshold of 50% target gene expression reported via the use of dissolvable microneedles.

The results set forth in the above examples indicate that disclosed meso devices effectively deliver siRNA to relevant regions of the skin with an efficiency (up to 80% inhibition) that, if translatable to human subjects, may offer relief to patients suffering from debilitating monogenic skin disorders. In contrast to this, direct injection of unmodified siRNA with a hypodermic needle results in 33% decrease in reporter gene expression. Generally it is known that the use of microneedles significantly decreases pain associated as compared with intradermal injections inhuman studies.

It has to be understood that the above-described various types of compositions, are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, may be made without departing from the principles and concepts set forth herein.

The invention claimed is:

1. A method of transdermally delivering nucleic acid material to a subject, comprising:
   introducing nucleic acid material into a chamber of a motorized meso machine;
   flowing the nucleic acid material from the motorized meso machine onto a skin surface of a subject; and
   contacting the motorized meso machine to the skin surface of the subject for a period of time sufficient to deliver the nucleic acid material into the skin surface of the subject.

2. The method of claim 1, wherein the nucleic acid material is siRNA.

3. The method of claim 1, wherein the nucleic acid material is sd-siRNA.

4. The method of claim 1, wherein the period of time is at about 5 seconds to about 20 seconds.

5. The method of claim 4, wherein the period of time is about 5 seconds.

6. The method of claim 4, wherein the period of time is about 20 seconds.

7. The method of claim 1, wherein the period of time is about 7 seconds to about 15 seconds.

8. The method of claim 7, wherein the period of time is about 7 seconds.

9. The method of claim 7, wherein the period of time is about 15 seconds.

10. The method of claim 1, wherein the subject is a human.

11. The method of claim 1, wherein the nucleic acid is suspended in a solution.

12. The method of claim 11, wherein the solution is a phosphate buffer solution.

13. The method of claim 1 further comprising adjusting a depth of penetration of needles of the meso machine.

14. The method of claim 1, further comprising adjusting a rate of oscillation of needles of the meso machine.

15. The method of claim 1, wherein the motorized meso machine includes needles that deliver the nucleic acid material into the skin surface at a depth of about 25 microns to about 3 mm.

16. The method of claim 15, wherein the motorized meso machine includes needles that deliver the nucleic acid material into the skin surface at a depth of about 25 microns.

17. The method of claim 15, wherein the motorized meso machine includes needles that deliver the nucleic acid material into the skin surface at a depth of about 3 mm.

18. The method of claim 1, wherein the step of contacting the motorized meso machine to a skin surface of a subject for a period of time sufficient to deliver the nucleic acid material into the skin surface of the subject is repeated.

19. The method of claim 18, wherein the step of contacting the motorized meso machine to a skin surface of a subject for a period of time sufficient to deliver the nucleic acid material into the skin surface of the subject is repeated on the same skin area.

20. The method of claim 18, wherein the step of contacting the motorized meso machine to a skin surface of a subject for a period of time sufficient to deliver the nucleic acid material into the skin surface of the subject is repeated on an adjacent skin area.

* * * * *